US00PP12234P2

(12) United States Plant Patent
Drewlow

(10) Patent No.: US PP12,234 P2
(45) Date of Patent: Nov. 27, 2001

(54) NEW GUINEA IMPATIENS PLANT NAMED 'OVATION BRIGHT PINK'

(75) Inventor: Lyndon W. Drewlow, Lompoc, CA (US)

(73) Assignee: Oglevee, Ltd., Connellsville, PA (US)

( * ) Notice: Subject to any disclaimer, the term of this patent is extended or adjusted under 35 U.S.C. 154(b) by 0 days.

(21) Appl. No.: 09/550,513

(22) Filed: Apr. 17, 2000

(51) Int. Cl.[7] ..... A01H 5/00

(52) U.S. Cl. ..... Plt./318

(58) Field of Search ..... Plt./318

*Primary Examiner*—Bruce R. Campell
*Assistant Examiner*—Anne Marie Grünberg
(74) *Attorney, Agent, or Firm*—Webb Ziesenheim Logsdon Orkin & Hanson, P.C.

(57) ABSTRACT

A distinct cultivar of Impatiens plant named Ovation Bright Pink, characterized by its pink flower color, bright green leaves, early flowering, long-lasting flowering, self-branching and vigorous habit.

1 Drawing Sheet

The present invention relates to a new and distinctive cultivar of Impatiens plant, botanically known as *Impatiens Hawkeri*, commercially known as New Guinea Impatiens, and known by the cultivar named 'Ovation Bright Pink'. Ovation Bright Pink was developed in a controlled breeding program by crossing Mikkelsen Seedling No. 94-857-1 (seed parent) with Mikkelsen Seedling No. 95-1105-1 (pollen parent). Both parents are proprietary breeding lines which have not been sold or made publicly available in this country.

Asexual reproduction carried out by the inventor in Lompoc, Calif. by terminal or stem cuttings has shown that the unique features of this new Impatiens are stabilized and are reproduced true to type in successive propagations.

The following combination of characteristics distinguish the new Impatiens from both its parent varieties and other cultivated Impatiens of this type known and used in the floriculture industry:

1. Ovation Bright Pink has a flower color of Red-Purple Group 58C while Electric Pink (U.S. Plant Pat. No. 8,399) flowers are more of a rose pink of Red-Purple Group 58B in color and Dark Delias (U.S. Plant Pat. No. 9,139) is a salmon-pink of Red Group 55A.

2. Ovation Bright Pink has intermediate flower size with 6.5 to 7.0 cm diameter flowers with Dark Delias having smaller flowers at 5.5 to 6.0 cm and the flowers of Electric Pink larger at 7.0 to 7.5 cm.

3. Ovation Bright Pink has a mound growth habit while Electric Pink and Dark Delias are more upright growing and taller.

4. Ovation Bright Pink has a yellow-green pedicel with Dark Delias and Electric Pink each having a red-purple pedicel.

5. Ovation Bright Pink has a spur with a red-purple cast and green tip, Dark Delias has a red-purple spur with green tip, and Electric Pink has a red-purple spur and tip.

6. Ovation Bright Pink has bright green leaves with Dark Delias having deep green leaves and Electric Pink having dark green leaves with a slight cast of red-purple.

7. Ovation Bright Pink and Dark Delias have similar sized leaves at 8.5 to 9.5 cm long and Electric Pink has longer leaves at 11.0 to 12.0 cm.

8. Ovation Bright Pink does not hav an eye in center of flower while Electric Pink and Dark Delias each have a carmine eye.

9. Ovation Bright Pink has a yellow-green midrib on underside of leaves while Electric Pink and Dark Delias each have a red-purple midrib on underside of leaves.

The accompanying colored photograph illustrates the overall appearance of this cultivar taken as a face view of the plant and showing the colors as true as it is reasonably possible to obtain in a colored reproduction of this type.

The following is a detailed description of my new cultivar, based on plants produced in greenhouses in Lompoc, Calif. during the Fall–Winter season of the year. Plants were grown in 15 cm pots and measurements were taken 20 weeks after rooted cuttings were planted. Height measurements were taken from the soil line of the container. The plants were grown at 16° C. night temperatures, under 3000 to 4000 foot candles of light and 200 ppm nitrogen, 75 ppm potassium, and 200 ppm phosphorous with nutritional trace elements added. Habit of growth, foliage coloration, leaf variegation, size of leaves, and flower size will be greatly influenced by nutritional and environmental conditions.

Color references are made to The Royal Horticultural Society Colour Chart except where general terms of ordinary dictionary significance are used.

Parentage: A controlled cross between female parent Mikkelsen Seedling No. 94-857-1 and male parent Mikkelsen Seedling No. 95-1105-1.

Propagation:

(*A*) *Type cutting.*—Stem tip 15 mm long will develop to 4 to 5 cm long in 18 to 21 days.

(*B*) *Time to root.*—8–10 days at 23° C. summer; 10–12 days at 20° C. winter.

(*C*) *Rooting habit.*—Heavy, fiborous.

Plant description:

(*A*) *Form and habit of growth.*—Mounded, self-branching, intermediate in height, flowers open over the top of leaf canopy; continuous flowering; vigorous growing flowering herb. Average height is 18 to 22 cm and average width is 40 to 45 cm. Internode length is 5 to 6 cm but is highly variable. Pedicel is Yellow-Green Group 148C, stem is Yellow-Green Group 146D with a Greyed-Purple Group 184D cast, and internode is Yellow-Green Group 146D with a Greyed-Purple Group 184D cast. Pedicel length is 4.5 cm.

(*B*) *Foliage description.*—Bright green with light green midrib and no leaf variegation. (1) Size: 8.5 to 9.5 cm long and 3.0 to 3.5 cm wide on average mature leaf. (2) Shape: Lanceolate with acuminate apex and acute base. (3) Texture: Both upper and lower surfaces are glabrous. (4) Margin: Finely serrated with fine cilia. (5) Color: Young foliage, top side is Yellow-Green Group 147A, underside is Yellow-Green Group 147B; Mature foliage, top side is Yellow-Green Group 147A, underside is Yellow-Green Group 148B. (6) Venation: Pinnate, upper side is Yellow-Green Group 146A and lower side is Yellow-Green Group 146B. (7) Young midrib is Yellow-Green Group 146C and mature midrib is Yellow-Green Group 148C.

(*C*) *Branching.*—The branching is naturally occurring. Lateral branching at base: 5 or more lateral branches. Lateral branch length is 15 to 18 cm but is highly variable.

Flowering description:

(*A*) *Flowering habits.*—Flowers continuously from leaf whorl in a progressively orderly manner with one flower per leaf axil. When the last flower in a leaf whorl opens the first flower in the leaf whorl above starts to open. It takes 5 to 7 days for a mature bud to fully open and the flower may last two weeks or longer depending on the environment. The time to first flower is approximately 8 weeks from root cuttings. The flowers are self-cleaning.

(*B*) *Natural flowering season.*—Indeterminant and continuous; quantity of flowering increases with increasing levels of light.

(*C*) *Flower bud.*—Ellipsoidal; flowers perfect; spur is 4.0 cm long on mature bud, with the throat behind the ovary and originating from the major sepal. Bud length is 16 to 18 mm and bud diameter is 13 mm. Spur is Greyed-Purple Group 185C, spur tip is Yellow-Green Group 146C, and flower bud is Red Group 54B just before opening.

(*D*) *Flowers borne.*—On individual 4.5 cm long yellow-green pedicels from a whorl of usually four leaves. Flowering progressively around the whorls as buds and leaves develop. Leaf axils have one flower each.

(*E*) *Quantity of flowers.*—Numerous because of self-branching nature of plant and the long-lasting flower characteristic.

(*F*) *Diameter of flower.*—6.5 to 7.0 cm. Flower Depth: 5 mm.

(*G*) *Petals.*—(1) Shape: Heart, keel petals are largest. (2) Color: Top side in winter when opening is Red-Purple Group 58C, fading is not apparent; underside is Red-Purple Group 62A. (3) Number of petals: Five. (4) Size of petals: Standard: 4.5 cm wide and 3.0 cm long, two equal lobes with shallow cut. Wings: 3.5 cm wide and 3.0 cm long, two unequal lobes with shallow cut. Keel: 4.5 cm wide and 3.5 cm long, two unequal lobes with deep cut.

(*H*) *Reproductive organs.*—(1) Stamens: Five in number. (a) Anther: Hooded shape, color is Yellow-White Group 158A. (b) Pollen color: Yellow-White Group 158C. (2) Pistils: (a) Stigma: Five, segmented column, color is White Group 155B. (b) Style color: White. (c) Ovaries: Five in number, size is 7 mm when immature, color is Yellow-Green Group 146A.

(*I*) *Fertility.*—The plants are fertile, but do not normally set seed under greenhouse or garden conditions, unless in a controlled crossing program. Disease resistance: No significant disease or insect problems seen to date.

OTHER IMPORTANT CHARACTERISTICS

1. Self-branching, early flowering nature allows cultivar to be grown in 10 cm pots but is also vigorous enough to be grown in 15 to 25 cm containers as well.

2. Minimal fading of older flowers, large overlapping petals result in a round flower that produces an attractive floral display.

3. Has shown the ability to tolerate both high temperatures and full sun and continue to bloom as demonstrated in Connellsville, Pa. summer trials and to bloom as well with cool night temperatures (5 to 10° C.) as demonstrated in outdoor trials in Lompoc, Calif., thus, extending the growing season.

I claim:

1. A new and distinct variety of Impatiens plant named Ovation Bright Pink, as illustrated and described.

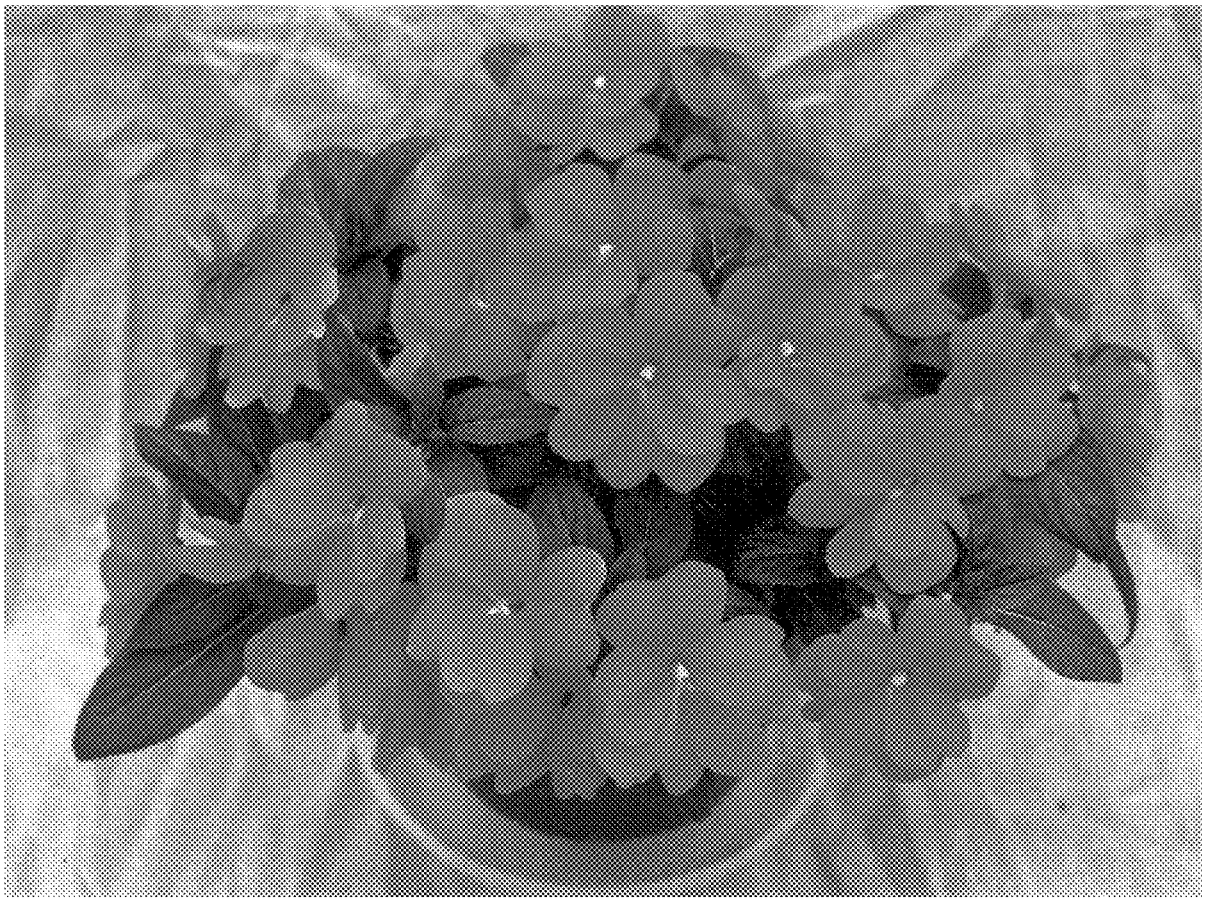

* * * * *